(12) United States Patent
Ladebeck et al.

(10) Patent No.: US 7,218,112 B2
(45) Date of Patent: May 15, 2007

(54) COMBINED MR/PET SYSTEM

(75) Inventors: Ralf Ladebeck, Erlangen (DE); Wolfgang Renz, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 210 days.

(21) Appl. No.: 11/127,831

(22) Filed: May 12, 2005

(65) Prior Publication Data

US 2006/0293580 A1 Dec. 28, 2006

(51) Int. Cl.
*G01V 3/00* (2006.01)

(52) U.S. Cl. .................. 324/318; 324/300; 600/411

(58) Field of Classification Search ........... 324/318, 324/322, 300; 600/407, 411
See application file for complete search history.

(56) References Cited

U.S. PATENT DOCUMENTS

| | | | |
|---|---|---|---|
| 4,939,464 A * | 7/1990 | Hammer | 324/318 |
| 6,946,841 B2 * | 9/2005 | Rubashov | 324/318 |
| 2003/0090267 A1 | 5/2003 | Rubashov | |
| 2005/0113667 A1* | 5/2005 | Schlyer et al. | 600/411 |
| 2006/0052685 A1* | 3/2006 | Cho et al. | 600/407 |

OTHER PUBLICATIONS

"Simultaneous PET and MR imaging", Phys. Med. Biol. 42 (1997) 1965-1970.
"A study of artifacts in simultaneous PET and MR imaging using a prototype MR compatible PET scanner", Phys. Med. Biol. 44 (1999) 2015-2027.
"Imaging Systems for Medical Diagnostics", Krestel, pp. 70-73, 458-481 (1988).
"Physical Principles and Technology of Clinical PET Imaging," DW Townsend, Mar. 2004, vol. 33, No. 2, Annals Academy of Medicine, 13 pages.
Siemens Medical, "Magnets, Spins, and Resonances" An introduction to the basics of Magnetic Resonance, Siemens Medical Solutions, 2003, 226 pages.

* cited by examiner

*Primary Examiner*—Louis M. Arana
(74) *Attorney, Agent, or Firm*—Brinks Hofer Gilson & Lione

(57) ABSTRACT

A combined magnetic resonance (MR) imaging and positron emission tomography (PET) system is provided. In one embodiment, a system is provided comprising a radiofrequency (RF) antenna and an RF screen spaced apart from one another to create an RF field reflux zone. The RF screen comprises a plurality of openings, and a plurality of a scintillator crystals are positioned in the plurality of openings in the RF screen such that at least a portion of the plurality of scintillator crystals are positioned in the RF field reflux zone. Other embodiments are provided, and each of the embodiments described herein can be used alone or in combination with one another.

20 Claims, 1 Drawing Sheet

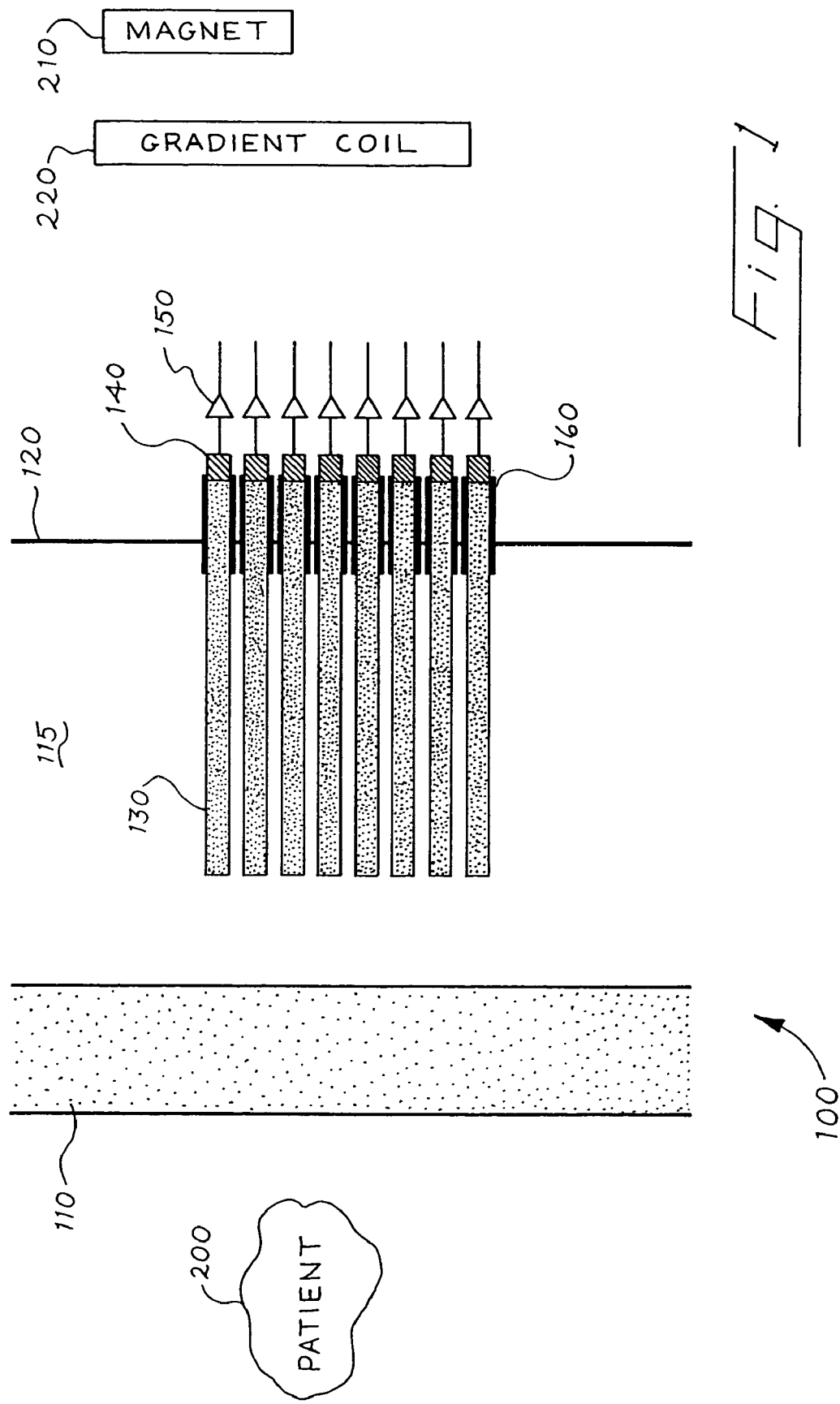

COMBINED MR/PET SYSTEM

BACKGROUND

It is often desired to combine magnetic resonance (MR) imaging and positron emission tomography (PET) in one unit to merge the high-resolution anatomical images provided by MR with functional information provided by PET. One difficulty in making a combined MR/PET system is that the RF transmit antenna of the MR system can produce deleterious effects on the photodetection electronics of the PET system. To avoid these deleterious effects, an RF screen (e.g., a continuous layer of copper) can be used to shield the photodetection electronics of the PET system from an RF antenna by placing all of the components of the PET system on the opposite site of the RF screen from the RF antenna. With this design, a larger-diameter gradient coil would be needed to provide the space needed for the components of the PET system. This greatly increases production costs, as the radial space inside a magnet tunnel is restricted and expensive. Another disadvantage to this design is that, because the RF screen is between the patient and the PET detector, the RF screen can attenuate gamma radiation emitted from the patient before it reaches the PET detector.

There is a need, therefore, for a combined MR/PET system that overcomes these problems.

SUMMARY

The present invention is defined by the following claims, and nothing in this section should be taken as a limitation on those claims.

By way of introduction, the below embodiments describe a combined magnetic resonance (MR) imaging and positron emission tomography (PET) system. In one embodiment, a system is provided comprising a radiofrequency (RF) antenna and an RF screen spaced apart from one another to create an RF field reflux zone. The RF screen comprises a plurality of openings, and a plurality of scintillator crystals are positioned in the plurality of openings in the RF screen such that at least a portion of the plurality of scintillator crystals are positioned in the RF field reflux zone. Other embodiments are provided, and each of the embodiments described herein can be used alone or in combination with one another.

The embodiments will now be described with reference to the attached drawings.

BRIEF DESCRIPTION OF THE DRAWINGS

FIG. 1 is a diagram of a combined MR/PET system of an embodiment.

DETAILED DESCRIPTION OF THE PRESENTLY PREFERRED EMBODIMENTS

Turning now to the drawings, FIG. 1 is a diagram of a combined MR/PET system 100 of an embodiment. This system 100 comprises a radiofrequency (RF) antenna 110 and an RF screen 120. The RF screen 120 is spaced apart from the RF antenna 110, and the area between the RF screen 120 and the RF antenna 110 is referred to as the "RF field reflux zone" 115. The system 100 also comprises a plurality of scintillator crystals 130, a plurality of light detectors 140 coupled with the LSO crystals 130, and a plurality of preamplifiers 150 coupled with the APDs 140. Scintillator crystals 130 can take any suitable form, including, but not limited to, thallium-activated sodium iodide (NaI(Tl)) crystals, bismuth germanate (BGO) crystals, gadolinium oxyorthosilicate (GSO) crystals, and lutetium oxyorthosilicate (LSO) crystals. Also, the light detectors can take any suitable form, including, but not limited to, avalanche photodiodes (APDs), position-sensitive avalanche photodiodes (APDs), Geiger-mode operated diodes, and silicon photomultiplier tubes (PMTs). In a presently preferred embodiment, the scintillator crystals 130 are lutetium oxyorthosilicate (LSO) crystals, and the light detectors 140 are avalanche photodiodes (APDs). As used herein, the phrase "coupled with" means directly coupled with or indirectly coupled with through one or more named or unnamed components. FIG. 1 can be considered a cross section (or cut-out) of an MR-PET system. As shown diagrammatically in FIG. 1, to the left of the RF antenna 110 would be a base upon which an examination object (normally a patient 200) would rest and to the right of the preamplifiers 150 would be other components of the MR system, such as a magnet 210 and a gradient coil 220.

In FIG. 1, the RF antenna 110, RF screen 120, magnet 210, and gradient coil 220 are part of the MR system, and the LSO crystals 130, APDs 140, and preamplifiers 150 are part of the PET system. In operation, with PET, a positron-emitting radiopharmaceutical is introduced into the body of the patient 200. Each emitted positron reacts with an electron in the patient's body and causes an "annihilation event," which generates a pair of gamma rays (or quantums) emitted in opposite directions. Emitted gamma quantums reaching the LSO crystals 130 are transformed by the LSO crystals 130 into photons of visible light, which are detected and transformed into electrical signals by the APDs 140. The preamplifiers 150 amplify these electrical signals, which are used to generate a PET image. The PET system is a passive system because it only looks at the gamma quantums emitted from the patient 200 and does not transmit anything into the patient 200.

In contrast, the MR system is an active system. In operation, the magnet 210 magnetizes the patient 200, and the gradient coil 220 makes the static magnetic fields generated by the magnet 210 spatially varying in a controlled way to achieve spatial resolution for MR image reconstruction. The RF antenna 110 (or RF coil) comprises various electronics (e.g., capacitors, inductors, semiconductors), which transmit and receive RF signals to and from the patient 200. When pulses of RF magnetic field pulses are applied to the patient 200 by the RF antenna 110 in the presence of an applied static magnetic field, magnetic moments of nuclei in the patient 200 precess about the direction of the applied static magnetic field and subsequently, after the excitation is switched off, emit RF signals, which are detected by the RF antenna 110. An image of a slice of a patient can be calculated by applying suitable reconstruction algorithms to the data obtained from the received RF signals.

An RF antenna and a gradient coil can produce deleterious effects on one another. For example, RF power from an RF antenna can vanish into a gradient coil, and noise from a gradient coil can affect an RF antenna. An RF transmit antenna can also produce deleterious effects for the photodetection electronics of the PET system (e.g., APDs and preamplifiers). To avoid these deleterious effects, an RF screen can be used to shield a gradient coil and photodetection electronics of the PET system from an RF antenna. As discussed in the background section, if all of the components of the PET system are placed on the opposite site of the RF screen from the RF antenna, the production cost of the system would greatly increase, as a larger-diameter gradient coil and magnet would be needed to provide the space needed for the components of the PET system. Also, because the RF screen would be between the LSO crystals and the patient, the RF screen would attenuate gamma radiation emitted from the patient before it reaches the LSO crystals.

The system 100 in FIG. 1 avoids these problems by taking advantage of the fact that, while the APDs 140 and pre-amplifiers 150 are sensitive to RF signals, LSO crystals are not. In this embodiment, instead of having all of the components of the PET system be on one side of a continuous RF screen, the RF screen 120 comprises a plurality of openings, and the LSO crystals 130 are positioned within the openings in the RF screen 120, such that at least a portion of the LSO crystals 130 are positioned in the RF field reflux zone 115 between the RF screen 120 and the RF antenna 110. The LSO crystals 130 can protrude into the RF field reflux zone 115 because they do not interact with the RF field in this area. With this arrangement, the PET components that are sensitive to RF signals are placed behind the RF shield 120, while the components that are not sensitive to RF signal is placed at least partially in front of the RF shield screen.

One advantage of this embodiment is that it combines MR and PET modalities in a way that brings together the necessary components of MR and PET such that the components do not disturb one another while consuming as little space as possible. Integrating the LSO crystals 130 into the RF screen 120 while still holding the RF-sensitive PET electronics behind the RF screen 120 consumes less space than if all of the components of the PET system were behind the RF screen 120 without deteriorating the behavior of the PET electronics behind the RF screen 120. Placing the LSO crystals 130 in the radial space already required for the RF field reflux zone 115 instead of adding addition radial length to the system 100 saves radial space inside the MR scanner as compared to the design described in the background section. This results in a system that requires less production cost, as a small-diameter magnet and gradient coil are needed. As an alternative, using an unchanged gradient coil and magnet makes a larger patient tunnel possible. Further, because this embodiment avoids placing the RF shield in front of the LSO crystals 130, this embodiment avoids the gamma attenuation encountered in the design described in the background section.

With reference again to FIG. 1, to fully integrate the LSO crystals 130 into the RF screen 120, a plurality of cutoff waveguides 160 are preferably positioned between each LSO crystal 130 and its respective opening in the RF screen 120 to prevent the deterioration of the screening effect of the RF screen 120. The LSO crystals 130 are made of an insulating, non-conducting material, and the cutoff waveguides 160 are filled with a dielectric material and behave like a strongly-attenuating hole in the RF screen 120. This is the so-called cutoff waveguide effect. Depending on the applied frequencies, for certain diameters of these cutoff waveguides 160, no wave propagation is possible inside the cutoff waveguides 160 as long as they are filled with purely dielectric material. If, in these frequency ranges (several ten megahertz), the cutoff waveguides 160 have a diameter of a few millimeters, which correspond to the diameter of the LSO crystals 130, and a length of 10–20 millimeters, the cut-off condition is well-fulfilled, and they exhibit a high attenuation for RF frequencies wanting to travel from one side of the RF screen 120 to the other.

It is presently preferred that the scintillator crystals 130 comprise a length that is about the same as a length of the RF field reflux zone 115. For example, the length of the scintillator crystals 130 and the RF field reflux zone 115 can be between about 1 or 2 to 5 centimeters. In one implementation, the length of the LSO crystals 130 and the length of the RF field reflux zone 115 is about 2–3 centimeters, and the LSO crystals 130 protrude about two centimeters into the RF field reflux zone 115, thereby saving about two centimeters of radius as compared to a completely spatially-separate arrangement of components. The RF screen 120 is preferably a double-sided structure with ten microns of copper and 100 microns of PCB-board material. The RF screen preferably has slot structure to suppress gradient induced eddy currents. The cutoff waveguides 160 are preferably very thin aluminum or copper foil tubes wrapped around each LSO crystal 130. It is presently preferred that the cutoff waveguides comprise a length/diameter ratio of two or more, three or more, or four or more. For example, the cutoff waveguides can have a diameter of about 2 to 4 mm diameter and a length of about 5 to 20 mm. Preferably, the cutoff waveguides 160 are in contact with the RF screen 120 and the LSO crystals 130 with no gaps therebetween. The preamplifier (the first electronic stage) is approximately one centimeter long. In terms of manufacturing, it is presently preferred to drill holes of the appropriate diameter into the RF screen 120, pushing the cutoff waveguides 160 (i.e., tubes) in the holes, and soldering the contact ring of the RF screen 120 toward the tubes, so that the RF screen 120 cannot be penetrated by RF, only by light. Of course, other sizes, materials, and manufacturing steps can be used.

It is intended that the foregoing detailed description be understood as an illustration of selected forms that the invention can take and not as a definition of the invention. It is only the following claims, including all equivalents, that are intended to define the scope of this invention.

What is claimed is:

1. A system for performing magnetic resonance (MR) imaging and positron emission tomography (PET), the system comprising:

a radiofrequency (RF) antenna;

an RF screen comprising a plurality of openings, the RF screen being spaced apart from the RF antenna, thereby creating an RF field reflux zone between the RF antenna and the RF screen; and a plurality of scintillator crystals positioned in the plurality of openings in the RF screen, wherein at least a portion of the plurality of scintillator crystals are positioned in the RF field reflux zone.

2. The system of claim 1, wherein the scintillator crystals comprise lutetium oxyorthosilicate (LSO) crystals.

3. The system of claim 1, wherein the scintillator crystals comprise thallium-activated sodium iodide (NaI(T1)) crystals.

4. The system of claim 1, wherein the scintillator crystals comprise bismuth germanate (BGO) crystals.

5. The system of claim 1, wherein the scintillator crystals comprise gadolinium oxyorthosilicate (GSO) crystals.

6. The system of claim 1 further comprising a plurality of cutoff waveguides, each cutoff waveguide positioned between a respective scintillator crystal and opening in the RF screen.

7. The system of claim 6, wherein the cutoff waveguides comprise a length/diameter ratio of two or more.

8. The system of claim 6, wherein the cutoff waveguides comprise a length/diameter ratio of three or more.

9. The system of claim 6, wherein the cutoff waveguides comprise a length/diameter ratio of four or more.

10. The system of claim 1 further comprising a plurality of light detectors coupled with the plurality of scintillator crystals.

11. The system of claim 10 further comprising a plurality of pre-amplifiers coupled with the plurality of light detectors.

12. The system of claim 10, wherein the light detectors comprise avalanche photodiodes.

13. The system of claim 10, wherein the light detectors comprise position-sensitive avalanche photodiodes.

14. The system of claim 10, wherein the light detectors comprise Geiger-mode operated diodes.

15. The system of claim 10, wherein the light detectors comprise silicon photomultiplier tubes (PMTs).

16. The system of claim 1, wherein the scintillator crystals comprise a length that is about the same as a length of the RF field reflux zone.

17. The system of claim 9, wherein the length of the scintillator crystals and the RF field reflux zone is between about 2 to 5 centimeters.

18. The system of claim 1, wherein the RF field reflux zone comprises a length of about 1 to 5 centimeters.

19. The system of claim 1 further comprising a gradient coil.

20. The system of claim 1 further comprising a magnet.

* * * * *